United States Patent [19]

Wilson

[11] Patent Number: 5,872,245
[45] Date of Patent: Feb. 16, 1999

[54] CONTINUOUS PROCESS FOR THE SYNTHESIS OF SUCROSE FATTY ACID ESTERS

[75] Inventor: Donald C. Wilson, San Jose, Calif.

[73] Assignee: Optima Technologies Group, San Jose, Calif.

[21] Appl. No.: 953,687

[22] Filed: Sep. 30, 1992

[51] Int. Cl.$^6$ .......................... C07H 13/02; C07H 13/06; C07H 1/00; C07H 1/06

[52] U.S. Cl. .......................... 536/119; 536/115; 536/120; 536/124

[58] Field of Search .................... 536/119, 115, 536/120, 124

[56] References Cited

U.S. PATENT DOCUMENTS

| | | | |
|---|---|---|---|
| 3,689,461 | 9/1972 | Balint et al. | 422/134 |
| 3,963,699 | 6/1976 | Rizzi et al. | 536/119 |
| 4,298,730 | 11/1981 | Galleymore et al. | 536/119 |
| 4,334,061 | 6/1982 | Bossier | 536/115 |
| 4,517,360 | 5/1985 | Volpenhein | 536/119 |
| 4,518,772 | 5/1985 | Volpenhein | 536/119 |
| 4,966,966 | 10/1990 | Wada et al. | 536/119 |
| 4,968,791 | 11/1990 | De Lier | 536/119 |
| 4,973,682 | 11/1990 | Willems | 536/119 |
| 5,043,438 | 8/1991 | Vlaardingen | 536/119 |

FOREIGN PATENT DOCUMENTS 349059  1/1990  European Pat. Off. .

OTHER PUBLICATIONS

Rizzi and Taylor, "A Solvent–Free Synthesis of Sucrose Polyester," *Journal of the American Oil Chemist's Society*, vol. 55, pp. 398–401 (1978).

Fuege, Zeringue, Weiss and Brown, "Preparation of Sucrose Esters By Interesterification," *Journal of the American Oil Chemist's Society*, vol. 47, pp. 56–60 (1970).

Felder et al., Elementary *Principles of Chemical Process*, p. 82 (Wiley 1978).

McCabe and Smith, Unit Operations of Chemical Engineering, 3d Ed., p. 66 (McGraw–Hill, 1976).

*Primary Examiner*—Douglas W. Robinson
*Assistant Examiner*—Everett White
*Attorney, Agent, or Firm*—The Kline Law Firm

[57] ABSTRACT

This present invention pertains to a process for the synthesis of sucrose fatty acid esters by reacting sucrose and a purified specific fatty acid ester under substantially solvent free conditions in the presence of a transesterification stationary catalyst and mechanical emulsification. The process is continuous, yielding selected individual products of separated simple sucrose fatty acid esters of mono-, di-, tri- and polyesters while recycling the unwanted ester fractions, the unreacted sucrose and fatty acid ester.

20 Claims, 2 Drawing Sheets

* Ⓐ = ANALYSIS, GAS CHROMATOGRAPH, LIQUID CHROMATOGRAPH OR TEMPERATURE/PRESSURE RELATIONSHIP MEASUREMENT.

5,872,245

CONTINUOUS PROCESS FOR THE SYNTHESIS OF SUCROSE FATTY ACID ESTERS

BACKGROUND—FIELD OF INVENTION

This invention pertains to a process for the synthesis of sucrose fatty-acid esters by reacting sucrose and a purified specific component fatty-acid ester under substantially solvent free conditions in the presence of a transesterification stationary catalyst and mechanical emulsification. The process comprises a continuous process for separating mono, di, tri and poly esters into individual products of variable HLB values by separation and recycling the unreacted sucrose and fatty-acid ester.

BACKGROUND—DESCRIPTION OF PRIOR ART

The food and pharmaceutical industries are currently turning their attention to polyol esters for use as low calorie fats and pharmaceutical agents. It has been found that these pharmaceutical agents can be used to lower blood cholesterol levels. They can also be used for treating hypercholesterolemia as described in U.S. Pat. No. 4,241,054, Volpenhein and Jandacek, issued Dec. 23, 1980 and U.S. Pat. No. 4,264,583, Jandacek, issued Apr. 28, 1981 (treatment of gallstones).

The desire to produce poly esters for these uses requires that they be produced in high yields and purities. Historically, to attain the poly esters, a mutual solvent solubilizing a polyol and esters of long chain fatty acids has been required to produce a homogeneous reaction medium in the presence of a transesterification catalyst. Most of the methods that exist today involve batch processes that use solvents and produce a single product that is of "mixed" esters. While some of these processes are automated and solvent free, they are nothing more than variations of the basic batch process. Where final product quality control is based on various combinations of excess reactants (non-stoichiometric) and lengthy processing times.

Efforts are currently being directed towards producing automated systems that have high yields of high purity which contain no solvent or are virtually solvent free. Since most of the solvents that have been used are toxic, they must either be completely removed (which adds to the expense of the equipment and final product) or not used at all. To date no one has been able to introduce a process, or equipment for the process, that will provide continuously high yields and purities of the sucrose or polyol esters. This process addresses the issues of high yields and purities while producing the final product on a continuous basis. This continuous basis approach (continuously recycling the unreacted ingredients) lowers the costs of the final product through less waste production and handling, while increasing the polyol ester yield and purity.

Processes for the synthesis of sucrose fatty acid esters in substantially solvent free batch and semi-batch systems as state above currently exist. Prior art is described in U.S. Pat. Nos. 5,043,438, 4,973,682, 4,968,791, 4,966,966, 4,517,360, 4,518,772, 3,963,699 and European Patent numbers 0 256 585, 0 254 374 and 0 301 684.

A major problem in the prior art for syntheses of sucrose fatty acid esters is the heterogeneous failure of the reactant mixture at the start of the transesterification reaction. The reactants properties caused partial or full de-mixing of the reactant mixture. This is undesirable generally and prohibitive to the attaining of the final products in reasonable time frames. To overcome this problem of de-mixing, U.S. Pat. No. 5,043,438 added emulsifiers. These emulsifiers create a macroscopically homogeneous starting mixture. Soaps are commonly used, however the use of soaps is not always desirable because of the resulting viscosity problems.

In U.S. Pat. No. 5,043,438 an initial reaction stage is first established in a first reaction zone. After the initial reaction has taken place and reaches steady state, it is then sent to a second reaction zone in which the reaction mixture from the first zone is further reacted. This process is a partially continuous batch process where the mixer is first reacted in an initiating batch and then moved on to secondary batch processors to be further reacted. It is only a partially continuous process in seeding the reaction as claimed.

The batch type process in U.S. Pat. No. 5,043,438 has many drawbacks. Major among them is the quality of the final product. In a batch process the quality of the final product is greatly affected by the processing time or variations of ingredient ratios at the batch's initiation. Production goals are not detectable until the batch washing is completed at which time the final product's quality and quantity are determined. This batch process relies heavily on chemicals to force the reactions. These chemicals must later be removed with other chemicals (solvents) and in some cases handled as noxious waste. This type of batch processing also can only produce one product at a time, which is generally a mixture of varying degrees of esterified polyol containing a variety of fatty acid radicals.

In addition the process described by U.S. Pat. No. 5,043,438 is a low polyol conversion process. It ideally operates at a polyol conversion rate of 15 to 30 percent, with 25 percent being ideal. This process is too cost prohibited to produce polyol conversions over 60 percent. Typically this type of process will produce yields in the range of 10 to 40 percent. The process also relies on using an emulsifier, such as alkali metal alkyl sulphates, to produce the reactants. The process also uses stripping agents such as hexane to reduce the lower-alkyl alcohol partial vapor pressure, using 1000 to 4000 liters per kilogram of reaction mixture. The process also works better in the earlier stages if a stripping agent such as hexane in quantities of 30 to 700 liters per kilogram are used. The use of such stripping agents as hexane require the disposal of noxious waste or additional hexane-polyol separation systems, and leave trace solvents in the final product. The process herein disclosed produces no by products other than the product it was designed to produce.

The process described in this application allows the user to produce individual degrees of esterification simultaneously on a continuous bases. These individual esters (i.e. dipalmitate sucrose) or combinations of individual esters of the same fatty acid radical can then be used to produce tailored products. It does not rely on stockpiling an inventory to produce other products. The process recycles the undesired ester fractions to produce an equilibrium product which is separated into individual ester product streams of mono-, di-, tri- and polyesters. This constant recycling allows the monoto react into di- while some of the poly- reverts back to tri-. There are eight equilibrium constants at work in this process where a specific fatty acid radical ester is a reactant. In the batch type systems that use mixtures of fatty acid radical esters (i.e. methylated vegetable oils), the equilibrium constants that are needed to be controlled are well over 2000, consequently there is no real control. This process, unlike batch processes currently used, has composition control of multiple ester product streams.

Referring to Mitsubishi's Ryoto Sugar Ester catalogue it can be seen in their examples given on page four that they do not separate into the individual esters as their product titles claim. Also the individual ester components, such as monoester are not separated out. The mono-, di-, tri- and polyesters remain combined together. The purest monoester they are able to attain is approximately seventy-five percent (i.e. S-1670).

U.S. Pat. No. 3,521,827 shows the preparation of a commercial grade sucrose polyester requiring only 50% to be of that ester, solvent free, using phenyl esters. During the reaction however, phenol is liberated. This is a highly toxic contaminant which becomes part of the product and is difficult to separate. As a result this patent process can not meet current demands for a synthesis of polyol fatty acid polyesters for the food industry.

U.S. Pat. No. 4,334,061, Brossier, III, issued Jun. 8, 1982, is for a method of separating and purifying polyesters formed by U.S. Pat. No. 3,963,699, Rizzi and Taylor, issued Jun. 15, 1976. U.S. Pat. No. 4,334,061 is only for separating and purifying the polyesters formed by Rizzi and Taylor. It can only separate one ester at a time using a carbonate compound at the conclusion of transesterification, unlike the process described in this application which separates the mono, di, tri and poly esters continuously.

Additional background information on previous art can be attained from U.S. Pat. No. 5,043,438, which goes into great detail describing previous art.

OBJECTS AND ADVANTAGES

Accordingly, several objects and advantages of the present invention are:

(a) to provide for a continuous process for the synthesis of sucrose fatty acid esters with an inert stripping gas rather than a toxic or noxious solvent;

(b) to provide for a continuous process for the synthesis of sucrose fatty acid esters with a polyol conversion of 95 percent or more;

(c) to provide for a continuous process for the synthesis of polyol esters using specific individual fatty acids ("simple" polyol esters);

(d) to provide for a continuous process for the synthesis of sucrose fatty acid esters without a pre-reactor;

(e) to provide for a continuous process for the synthesis of sucrose fatty acid esters in which no solvent is required;

(f) to provide for a continuous process for the synthesis of sucrose fatty acid esters separating them into mono-, di-, tri- and polyesters;

(g) to provide for a continuous process for the synthesis of sucrose fatty acid esters in the controlled forming of flakes, powder, bricks, sheets or pellets;

(h) to provide for a continuous process for the synthesis of sucrose fatty acid esters of up to 99.9% purity;

(i) to provide for a continuous process at elevated temperatures of 75 to 250 degrees centigrade;

(j) to provide for a continuous process using mechanical emulsifiers;

(k) to provide for a continuous process where the reactor can be operated in batch and continuous;

(l) to provide for a continuous process where the methylated ester comes from a continuous process;

(m) to provide for a continuous process where the methylated ester comes from a batch process;

(n) to provide for a continuous process where the catalyst is stationary;

(o) to provide for a continuous process where the preferred embodiment is methylated fatty acid esters as the intermediate step between the raw oil materials and the sucrose fatty acid ester product;

Further objects and advantages are to provide for a process that does not require extensive washing processes of a crude sucrose fatty acid ester for purification and the related production of noxious waste. A process that allows for vegetable oil, tallow, fatty acid or methylated esters to be used as the raw ingredients for the continuous process for the synthesis of sucrose fatty acid esters. The system separates the final products into the different degrees of esterification of individual fatty acid esters at elevated temperatures by density. Since the reactant ester is of specific fatty acid ester, the process is not prone to failure as U.S. Pat. No. 5,043,438. This results in a more successful process than Pat. No. 5,043,438 where the methylated ester reactants are derived from a mixture of fatty acids (a function of vegetable oil used). A further object of this process is to provide a synthesis of polyol fatty acid polyesters which does not use a toxic solvent or generate noxious waste that later has to be removed and treated. Since this process produces no noxious waste and uses no solvent that later would have to be removed, it can be used in the food industry. This process was developed to produce sucrose fatty-acid esters of high purity at high yields that are solvent free and can be used in the food industry, cosmetic, chemical and pharmaceutical industries.

DRAWING FIGURES

In FIG. 1 the general process schematic is shown for the continuous process for the synthesis of sucrose fatty acid esters.

In FIG. 2 the process schematic is shown for the continuous process for the synthesis of high purity pelletized sucrose di-palmitate (HLB 7).

DETAILED DESCRIPTION OF THE INVENTION

Figure 1:
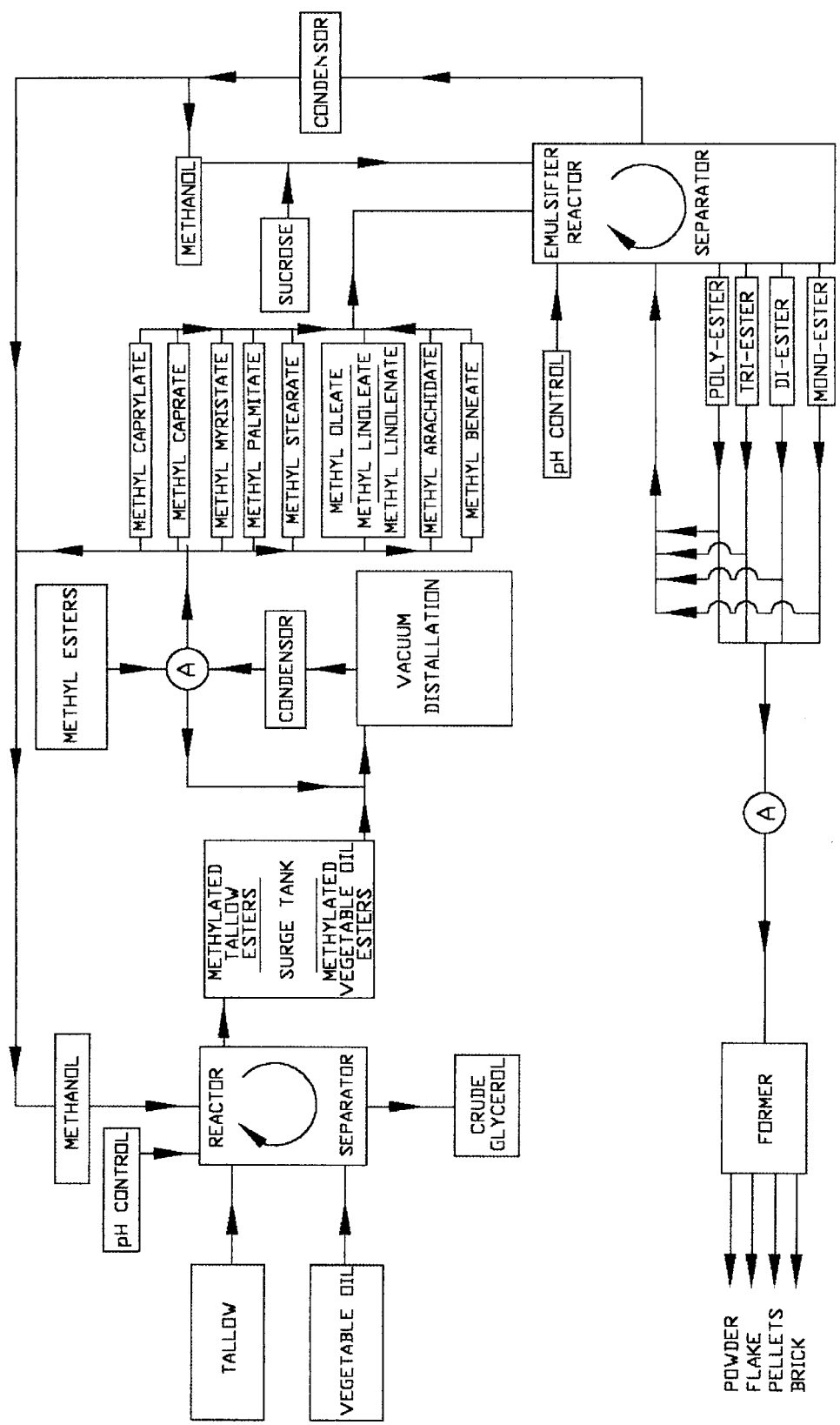

Referring to FIG. 1, a generalized process schematic is shown for tallow, vegetable oil or methyl esters as the fatty acid sources. In this description methanol is used as the low molecular weight alcohol in the intermediate transesterification reaction. This process applies to both continuous or batch systems, and it is assumed that the feedstocks are all of such a quality that they can be used without further upgrading.

The triglycerides from vegetable oil or tallow are well mixed with methanol continuously at elevated temperatures in an oxygen excluding vessel. The vessel content's pH is controlled with a methanol (or the same alcohol as used in the intermediate transesterification reaction) solution of sodium hydroxide to prevent the formation of any free fatty acids. Methyl fatty acid esters and glycerol are the products which are continuously separated into three density fractions:

The Heavy Fraction made up entirely of crude glycerol is removed as a by-product;

The Middlings Fraction made up of poorly separated glycerol, unreacted oil and poorly separated methyl esters is recycled through the mixing portion of the reactor-separator with the fresh feedstock of methanol and oil;

The Light Fraction made up of methyl esters and unreacted methanol is sent to the distillation surge tanks of methylated tallow esters and/or methylated vegetable oil esters.

If methylesters are the prime feedstock to this process then they will enter the system at this point after being analyzed for their purity. If the feedstock is a single fatty acid ester of sufficient purity then distillation will not be required and it can go directly to the appropriate storage tank.

The vacuum distillation in FIG. 1 can be continuous or batchwise. with the large number of ester fractions to be removed by distillation the batchwise method is the most practical when considering purity levels and initial capitol equipment requirements. During distillation the methyl esters are fractionated and stored in individual temperature controlled storage tanks for further processing as required. The number of ester fractions and their quantity will be a function of type and source of the edible oil feedstocks. The possible fractions are: methyl caprylate, methyl caprate, methyl laurate, methyl myristate, methyl palmitate, methyl stearate, methyl arachidate and methyl benenate. Methyl oleate, methyl linoleate and methyl linolenate are distilled as a combined fraction and are stored together as methyl unsaturated fatty acid esters.

An ester from one of the single ester storage tanks and an appropriate amount of methanol dissolved sucrose is continuously fed to the mechanical emulsifier-reactor-separator. The ester, sucrose and recycling materials are passed through the mechanical emulsifier at elevated temperature (75 to 250 degrees centigrade and pressure (greater than one atmosphere). Again the reactor vessel's pH is controlled with very small quantities of methanol dissolved sodium hydroxide. The resulting emulsion is passed over the stationary catalyst surface of heavy metal (Cu, Zn, Sn, Pb or combinations thereof) where the closed vessel methanol atmosphere pressure is controlled by a condenser. The resulting products, in a liquid state, are separated according to their density in the constant temperature controlled chamber: unreacted sucrose, sucrose monoester, sucrose diester, sucrose triester, sucrose polyester and unreacted methyl ester. The unreacted sucrose and methyl ester are recycled through the reactor's mechanical emulsifier with the sucrose and methyl ester feed. The various degrees of sucrose fatty acid esters can be stored in individual heated surge tanks and/or drawn off individually (or in combinations) based on forming equipment availability and final product demand. Those specific esters not required for products can be recycled with the unreacted sucrose and methyl ester. The fresh methyl ester and sucrose added to the recycling mixture is mandated by the products removed for forming or storage such that a constant mass and mole relationship is maintained in the emulsifier-reactor-separator;

The discharging sucrose fatty acid esters are in a liquid state and can be easily formed into various product configuration by cooling in the cast formers as bricks, pellets, flakes or crushing into powder.

Figure 2:
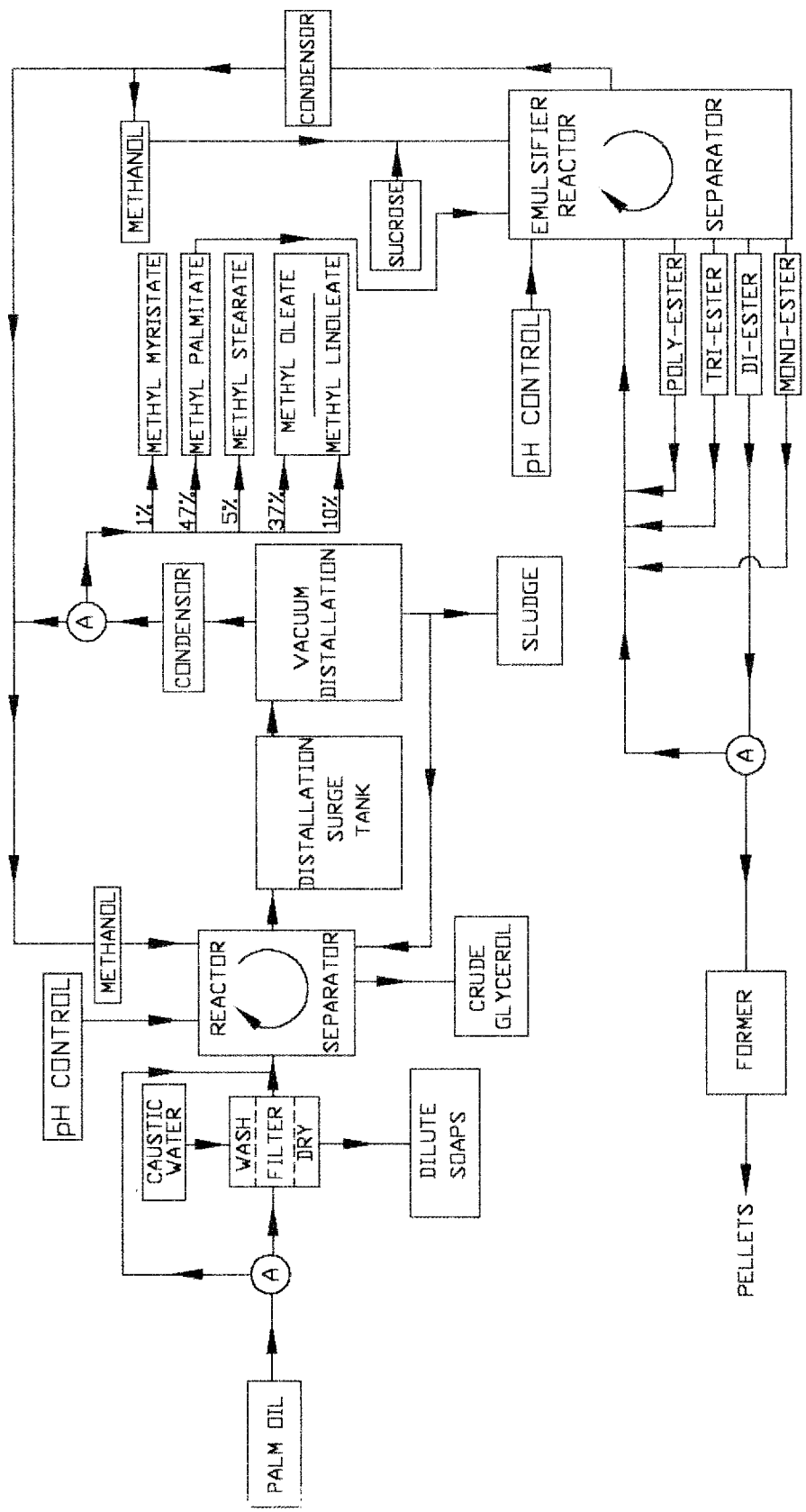

Referring to the process schematic shown in FIG. 2, refined Indonesian palm oil is used as the fatty acid source to produce sucrose di-palmitate ester having a hydrophillic-lipophillic balance (HLB) of seven. The palm oil is analyzed to determine its quality and if required it is washed with a caustic solution, filtered and dried to remove free fatty acids and water. A by-product of this washing is dilute soaps.

The quality refined oil then proceeds to the pH and temperature controlled reactor-separator where it is continuously mixed in a mechanical emulsifier with methanol to produce methyl esters (1% methyl myristate, 47% methyl palmitate, 5% methyl stearate, 37% methyl oleate and 10% methyl linoleate) and glycerol. The products are split up into three density fractions:

The Heavy Fraction made up entirely of crude glycerol is removed as a by-product;

The Middlings Fraction made up of poorly separated glycerol, unreacted palm oil (mono-, di-, and trigicerides) and poorly separated methyl esters is recycled through the reactor with the fresh feedstock of methanol and oil;

The Light Fraction made up methyl esters and unreacted methanol is sent to the distillation surge tank.

The vacuum distillation in FIG. 2 is a batchwise type. The mixture of methylated fatty acids from palm oil are periodically drawn from the continuously filling distillation surge tank into the vacuum distiller. The first product to be boiled off and condensed of the methylated ester mixture (Light Fraction) is the unreacted methanol which is returned to the methanol feedstock tank. The next component removed from the mixture is methyl myristate and this is routed to the appropriate temperature controlled storage tank for use at a later date (note that this rather small fraction will contain traces of low molecular weight "cracked" free fatty acids which will require redistillation after accumulating enough material to make a processing run). The third component, methyl palmitate, is directed towards the methyl palmitate storage tank which is being continuously withdrawn to produce the desired sucrose di-palmitate ester. The fourth component from the vacuum distiller is methyl stearate which is placed into storage for later processing. The fifth and sixth components both have similar boiling points and are stored together as unsaturated fatty acid esters (methyl oleate and methyl linoleate). The splits between the various methylated esters is determined by the distilling temperature and pressure relationship. The "bottoms", the undistilled oil remaining in the vacuum distiller is recycled back to the reactor-separator as mono-, di-, or triglyceride oils. Periodically the "bottoms" are discharged as sludge due to a high content of polymerized palm oil.

The methyl palmitate (continuously being drawn from the storage tank) is sent to the mechanical emulsifier-reactor with methanol dissolved sucrose to be mixed by the mechanical emulsifier. The resulting emulsion is passed over the stationary catalyst surface as described for FIG. 1. The resulting products are stratified in the separator into: unreacted sucrose, sucrose monoplamitate, sucrose dipalmitate, sucrose tripalmitate, sucrose polypalmitate and unreacted methyl palmitate. In this case of FIG. 2, the only desired product of dipalmitate sucrose (HLB7) is withdrawn from the separator. All of the other products are recycled through the reactor's mechanical emulsifier with the makeup material of one part sucrose and two parts methyl palmitate to compensate for the withdrawal of the dipalmitate sucrose (maintaining a constant mass in the continuous emulsifier reactor-separator unit).

The continual withdrawal of sucrose di-palmitate ester and the eight equilibrium constants for this single fatty acid ester and sucrose reaction will limit the quantities of non sucrose di-palmitate formed: the methyl palmitate will preferentially react with the sucrose and mono ester while the sucrose will preferentially react with the tri and poly esters in the presence of the methanol and stationary catalyst at elevated temperatures of 75 to 250 degrees centigrade.

The composition of the product from the process described in FIG. 2 is:

| SUCROSE DIPALMITATE, HLB 7 | |
|---|---|
| Sucrose Monopalmitate | 6.7% |
| Sucrose Dipalmitate | 71.0% |
| Sucrose Tripalmitate | 19.4% |

-continued

| | |
|---|---|
| Sucrose Polypalmitate | 2.5% |
| Free Sugars | <0.1% |
| Methyl Palmitate | <0.1% |
| Sucrose Monomyristate-Monopalmitate | 0.2% |
| Sucrose Monostearate-Monopalmitate | 0.2% |

The composition of other products derived from the processing of sucrose with methyl palmitate are:

SUCROSE MONOPALMITATE, HLB 18

| | |
|---|---|
| Sucrose Monopalmitate | 92.5% |
| Sucrose Dipalmitate | 7.1% |
| Sucrose Tripalmitate | 0.1% |
| Sucrose Polypalmitate | >0.1% |
| Free Sugars | 0.1% |
| Methyl Palmitate | <0.1% |
| Sucrose Monomyristate | 0.1% |
| Sucrose Monostearate | 0.1% |

SUCROSE TRIPALMITATE, HLB 3

| | |
|---|---|
| Sucrose Monopalmitate | 0.2% |
| Sucrose Dipalmitate | 23.1% |
| Sucrose Tripalmitate | 44.3% |
| Sucrose Polypalmitate | 31.8% |
| Free Sugars | <0.1% |
| Methyl Palmitate | 0.1% |
| Esters containing Myristic and Stearic Fatty Acids (est.) | 0.5% |

SUCROSE POLYPALMITATE, HLB 1

| | |
|---|---|
| Sucrose Monopalmitate | <0.1% |
| Sucrose Dipalmitate | 0.5% |
| Sucrose Tripalmitate | 7.5% |
| Sucrose Polypalmitate | 88.0% |
| Free Sugars | <0.1% |
| Methyl Palmitate | 3.2% |
| Esters containing Myristic and Stearic Fatty Acid (est.) | 0.8% |

Note for the analyses that Sucrose Polypalmitate is the ester mixture of Sucrose Tetra-, Penta-, Hexa-, Hepta-, and Octapalmitate.

SUMMARY, RAMIFICATIONS, AND SCOPE

Accordingly, the reader will see that this process for the synthesis of sucrose fatty acid esters produces esters of high purity and yield, while allowing for the use of raw ingredients of low quality. It does not produce noxious waste. Furthermore, the process has the additional advantages in that it raises the process for making sucrose fatty acid esters from an acquired skill to a technological level. It produces single species esters that can only be produced using this technology, whereas in a typical batch process many esters are produced at once in low quantities and quality.

This process can be computer controlled since it is producing single species esters (eight equilibrium constants) and not a combination of ester species and degrees of esterification (over a thousand equilibrium constants) as in a typical batch system. Using this process combined with computer technology allows this system to be utilized without years of trail and error by skilled technicians. This new process will allow the manufacturer to reduce their costs while increasing the quality and quantity of the final product by adapting to wide variations in the feedstock.

Although the description above contains many specificities, these should not be construed as limiting the scope of the invention, but as merely providing illustrations of some of the presently preferred embodiments of this invention. For example, this process allows for the production of sucrose fatty acid esters in various HLB levels. It minimizes by-products and waste materials.

Thus the scope of the invention should be determined by the appended claims and their legal equivalents, rather than by the examples given.

I claim:

1. A process for the synthesis of polyol fatty acid esters comprising the steps of:
    A. reacting ingredients of a polyol and a fatty acid ester of low molecular weight alcohol at a temperature of 75 to 250 degrees centigrade and a controlled pressure,
    B. separating the resulting equilibrium reaction products by their liquid density according to their degree of esterification, and
    C. recycling the unreacted ingredients; wherein
    said temperature and said pressure are set to values to yield an optimal percentage of desired products, while allowing an initial reaction percentage of the reactant mixture to remain low, said reaction percentage being maximized by multiple passes of the reactant mixture through a reaction zone.

2. The process according to claim 1 wherein: the fatty acid ester of low molecular weight alcohol ingredient is formed by:
    A. reacting edible oils with the low molecular weight alcohol condensate from the polyol fatty acid ester reaction,
    B. continuously separating glycerol, fatty acid ester of low molecular weight alcohol, and unreacted ingredients by density,
    C. recycling the unreacted ingredients for further reaction, removing the glycerol, and distilling the low molecular weight alcohol fatty acid ester into individual, simple, fatty acid radical fractions.

3. The process according to claim 1 wherein the polyol is glucose.

4. The process according to claim 1 wherein a low molecular weight alcohol that is esterified with the fatty acid ester ingredient is used as a polyol carrier.

5. The process according to claim 1 wherein the synthesis of polyol fatty acid esters is performed with the use of an inert stripping gas.

6. The process according to claim 1 wherein there is a recycling of unwanted polyol ester product density fractions with the unreacted ingredients.

7. The process according to claim 1 for the synthesis of polyol fatty acid ester with a polyol conversion rate of greater than 95 percent.

8. A process for the synthesis of sucrose fatty acid esters comprising:
    A. reacting a sucrose and a fatty acid at a temperature of 75 to 250 degrees centigrade and a controlled pressure,
    B. separating the resulting equilibrium reaction products by their liquid density according to their degree of esterification, and
    C. recycling the unreacted ingredients.

9. The process according to claims 1 or 8 wherein substantially no solvent is required.

10. The process according to claims 1 or 8 wherein the ingredients are mixed in a mechanical emulsifier.

11. A process for the synthesis of simple sucrose fatty acid esters comprising:
    A. reacting a mechanically emulsified mixture of sucrose and a substantially pure single fatty acid radical ester under solvent free conditions in the presence of a stationary transesterification catalyst, at a temperature of 75 to 250 degrees centigrade and a controlled pressure, B. continuously separating the resulting equilibrium reaction products by their liquid density into the final individual products of mono-, di-, tri-, and polyester according to their variable HLB values, and C. continuously recycling the unreacted sucrose and fatty acid ester density fractions.

12. The process according to claim 11 wherein:

the final product of sucrose polyester is additionally separated into tetra-, penta-, hexa-, hepta-, and octaester by density.

13. The process according to claims 1, 8 or 11 wherein:

the final liquid products are formed into bricks, pellets, sheets and flakes.

14. The process according to claims 1, 8 or 11 wherein:

there is a continuous final product withdrawal and a continuous makeup of ingredients.

15. The process according to claims 1 or 11 wherein the fatty acid ester is a methylated ester.

16. The process according to claims 1 or 11 wherein the fatty acid ester is an ethylated ester.

17. The process according to claim 11 wherein the fatty acid radicals used are substantially unmixed.

18. The process according to claim 11 wherein a stationary transesterification catalyst of heavy metals is used.

19. The process according to claims 1, 8 or 11 wherein the final products of different degrees of esterification are up to 99.9 percent purity.

20. The process according to claims 8 or 11 wherein the synthesis of sucrose fatty acid esters is performed with the use of an inert stripping gas.

* * * * *